(12) United States Patent
Schreiber et al.

(10) Patent No.: US 7,005,534 B2
(45) Date of Patent: Feb. 28, 2006

(54) METHOD FOR PRODUCING HYDROLYSIS-STABLE AMMONIUM NITRILES

(75) Inventors: Manfred Schreiber, Frankfurt (DE); Georg Borchers, Bad Nauheim (DE); Oliver Mogck, Burgkirchen (DE); Frank Weinelt, Burgkirchen (DE)

(73) Assignee: Clariant GmbH, Frankfurt (DE)

( * ) Notice: Subject to any disclaimer, the term of this patent is extended or adjusted under 35 U.S.C. 154(b) by 241 days.

(21) Appl. No.: 10/343,495

(22) PCT Filed: Aug. 1, 2001

(86) PCT No.: PCT/EP01/08883

§ 371 (c)(1),
(2), (4) Date: Sep. 30, 2003

(87) PCT Pub. No.: WO02/12175

PCT Pub. Date: Feb. 14, 2002

(65) Prior Publication Data

US 2004/0059148 A1    Mar. 25, 2004

(30) Foreign Application Priority Data

Aug. 4, 2000  (DE) .............................. 100 38 086

(51) Int. Cl.
*C07C 255/24*  (2006.01)
(52) U.S. Cl. ...................... 558/452; 558/378
(58) Field of Classification Search ................ 558/311, 558/378, 452
See application file for complete search history.

(56) References Cited

U.S. PATENT DOCUMENTS 6,498,133 B1 * 12/2002 Borchers et al. ............ 510/314

FOREIGN PATENT DOCUMENTS

| EP | 0 303 520 | 2/1989 |
| EP | 0 458 396 | 11/1991 |
| EP | 0 464 880 | 1/1992 |
| EP | 0 464 880 A1 * | 1/1992 |
| EP | 0 790 244 | 8/1997 |
| EP | 0 897 974 | 2/1999 |

OTHER PUBLICATIONS

English abstract for EP 0790244, Aug. 20, 1997.
English abstract for EP 0897,974, Feb. 24, 1999.

* cited by examiner

Primary Examiner—Johann Richter
Assistant Examiner—Ebenezer Sackey
(74) Attorney, Agent, or Firm—Richard P. Silverman

(57) ABSTRACT

The invention relates to a method for producing hydrolysis-stable ammonium nitriles by reacting a compound of formula (1), wherein $R^1$, $R^2$, and $R^3$ are identical or different and represent linear or branched $C_1$–$C_{24}$-alkyl groups, $C_2$–$C_{24}$-alkenyl groups, substituted or non-substituted benzyl or $C_1$–$C_4$-alkoxy-$C_1$–$C_4$-alkyl groups, or wherein $R^1$ and $R^2$, together with the nitrogen atom to which they are bonded, form a ring with 4 to 6 C-atoms which can be substituted with $C_1$–$C_5$ alkyl, $C_1$–$C_5$ alkoxy, $C_1$–$C_5$ alkanoyl, phenyl, amino, ammonium, cyano, cyanamino, chlorine or bromine and which can contain in addition to the nitrogen atom, instead of the carbon atoms, one or two oxygen or nitrogen atoms, a group N—$R^6$ or a group $R^3$—N—$R^6$, wherein R6 is hydrogen, $C_1$–$C_5$-alkyl, $C_2$–$C_5$-alkenyl, $C_2$–$C_5$-alkinyl, phenyl, $C_7$–$C_9$-aralkyl, $C_5$–$C_7$-cycloalkyl, $C_1$–$C_6$-alkanoyl, cyanomethyl or cyan, $R^4$ and $R^5$ are hydrogen, $C_1$–$C_4$-alkyl, $C_1$–$C_4$-alkenyl, $C_1$–$C_4$-alkoxy-$C_1$–$C_4$-alkyl, phenyl or $C_1$–$C_3$-alkylphenyl, preferably hydrogen, methyl or phenyl, $R^4$ especially meaning hydrogen when $R^5$ does not mean hydrogen, and X represents an anion; with an alkaline or ammonium salt of an alkane sulfonate, paraffin sulfonate, aryl sulfonate, alcohol sulfate or fatty acid alkyl carboxylate in the presence of water, at a high temperature (1)

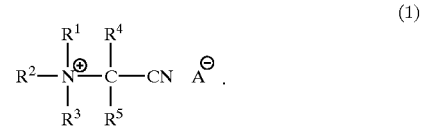

13 Claims, No Drawings

METHOD FOR PRODUCING HYDROLYSIS-STABLE AMMONIUM NITRILES

The present invention relates to a method for producing hydrolysis-stable ammonium nitrites by reacting ammonium nitrites with sulfonates.

Bleach activators are important constituents in compact detergents, stain-removal salts and machine dishwashing detergents. At temperatures as low as 40–60° C., they permit a bleaching result comparable with that of a boil wash by reacting with hydrogen peroxide-donors (in most cases perborates, percarbonates, persilicates and perphosphates) to release peroxy acids.

Many substances are known as bleach activators in the prior art. They are usually reactive organic compounds with an O-acyl or N-acyl group which, in alkaline solution together with a source of hydrogen peroxide, form the corresponding peroxy acids.

Representative examples of bleach activators are, for example, N,N,N',N'-tetraacetylethylenediamine (TAED), glucose pentaacetate (GPA), xylose tetraacetate (TAX), sodium 4-benzoyloxybenzenesulfonate (SBOBS), sodium trimethylhexanoyloxybenzenesulfonate (STHOBS), tetraacetylglucoluril (TAGU), tetraacetylcyanic acid (TACA), di-N-acetyldimethylglyoxine (ADMG) and 1-phenyl-3-acetylhydantoin (PAH).

Ammonium nitrites of the formula 1 form a particular class of cationic bleach activators. Compounds of this type and use thereof as bleach activators in bleaches are described in EP-A-0 303 520, EP-A-0 464 880, EP-A-0 458 396, EP-A-0 897 974 and EP-A-0 790 244.

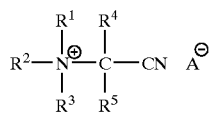

Formula 1 in which $R^1$, $R^2$, $R^3$ are identical or different and are linear or branched $C_1$–$C_{24}$-alkyl groups, $C_2$–$C_{24}$-alkenyl groups or are $C_1$–$C_4$-alkoxy-$C_1$–$C_4$-alkyl groups, substituted or unsubstituted benzyl, or in which $R^1$ and $R^2$ together with the nitrogen atom to which they are bonded form a ring having 4 to 6 carbon atoms, which may be substituted by $C_1$–$C_5$-alkyl, $C_1$–$C_5$-alkoxy, $C_1$–$C_5$-alkanoyl, phenyl, amino, ammonium, cyano, cyanamino, chlorine or bromine and which can contain in addition to the nitrogen atom, instead of carbon atoms, one or two oxygen or nitrogen atoms, a group N—$R^6$ or a group $R^3$—N—$R^6$, in which $R^6$ is hydrogen, $C_1$–$C_5$-alkyl, $C_2$–$C_5$-alkenyl, $C_2$–$C_5$-alkynyl, phenyl, $C_7$–$C_9$-aralkyl, $C_5$–$C_7$-cycloalkyl, $C_1$–$C_6$-alkanoyl, cyanomethyl or cyano, $R^4$ and $R^5$ are hydrogen, $C_1$–$C_4$-alkyl, $C_1$–$C_4$-alkenyl, $C_1$–$C_4$-alkoxy-$C_1$–$C_4$-alkyl, phenyl or $C_1$–$C_3$-alkylphenyl, preferably hydrogen, methyl or phenyl, where in particular $R^4$ is hydrogen if $R^5$ is not hydrogen, and A is an anion, for example chloride, bromide, iodide, fluoride, sulfate, hydrogen sulfate, carbonate, hydrogen carbonate, phosphate, mono- and dihydrogen phosphate, pyrophosphate, metaphosphate, nitrate, methylsulfate, phosphonate, methylphosphonate, methanedisulfonate, methylsulfonate or ethanesulfonate.

The synthesis of quaternized ammonium nitriles takes place in a known manner by reaction of a secondary amine with sodium cyanide and formaldehyde, and subsequent methylation with, for example, methyl chloride, benzyl chloride or dimethyl sulfate, or by reaction of secondary amines with chloroacetonitrile.

For the use of the ammonium nitriles as bleach activator in laundry detergents and cleaning compositions, the hygroscopicity of the ammonium nitriles and the sensitivity to hydrolysis in the presence of alkaline laundry detergent constituents and a correspondingly low storage stability associated therewith are highly disadvantageous.

EP-A-0 464 880 describes that the hygroscopicity of ammonium nitriles is influenced by the type and size of the anions. Ammonium nitriles with alkane- or paraffinsulfonate, arylsulfonate, primary alcohol sulfate, or fatty acid alkylcarboxylate as counterion are more stable than ammonium nitriles with conventional anions, such as, for example, chloride, nitrate or methosulfate. The specification teaches that ammonium nitriles with the counterions $RSO_3^-$, $RSO_4^-$ or $RCO_2^-$ are obtained by anion exchange from ammonium nitrile with chloride or methylsulfate as counterion. In this connection, the ammonium nitrile chloride or methylsulfate is dissolved in methanol/isopropyl alcohol and, by adding the sodium salt of a sulfonate, sulfate or carboxylate, the corresponding ammonium nitrile is precipitated.

Alternatively, a dry mixing of the ammonium nitrile having conventional anions with a sodium salt of a sulfonate, sulfate or carboxylate is proposed, where no actual anion exchange takes place and the resulting product sticks together and is only moderately stable.

The anion exchange by precipitation reaction in polar organic solvents, such as, for example, methanol and isopropanol, is disadvantageous for ecological and economic reasons; separating the solvent off from the precipitation product is complex.

Surprisingly, it has been found that the anion exchange, required for reducing the hydrolysis sensitivity and the hygroscopicity of ammonium nitrites, of conventional anions, for example chloride or methylsulfate for alkane- or paraffinsulfonate, arylsulfonate, primary alcohol sulfate, for example lauryl sulfate or fatty acid alkylcarboxylate, can take place in a simple manner in water.

The invention provides a method for producing hydrolysis-stable ammonium nitrites by reacting a compound of the formula 1

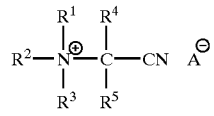

Formula 1 in which $R^1$, $R^2$, $R^3$ are identical or different and are linear or branched $C_1$–$C_{24}$-alkyl groups, $C_2$–$C_{24}$-alkenyl groups or are $C_1$–$C_4$-alkoxy-$C_1$–$C_4$-alkyl groups, substituted or unsubstituted benzyl, or in which $R^1$ and $R^2$ together with the nitrogen atom to which they are bonded form a ring having 4 to 6 carbon atoms, which may be substituted by $C_1$–$C_5$-alkyl, $C_1$–$C_5$-alkoxy, $C_1$–$C_5$-alkanoyl, phenyl, amino, ammonium, cyano, cyanamino, chlorine or bromine and which can contain in addition to the nitrogen atom, instead of carbon atoms, one or two oxygen or nitrogen atoms, a group N—$R^6$ or a group $R^3$—N—$R^6$, in which $R^6$ is hydrogen, $C_1$–$C_5$-alkyl, $C_2$–$C_5$-alkenyl, $C_2$–$C_5$-alkynyl, phenyl, $C_7$–$C_9$-aralkyl, $C_5$–$C_7$-cycloalkyl, $C_1$–$C_6$-alkanoyl, cyanomethyl or cyano, $R^4$ and $R^5$ are hydrogen, $C_1$–$C_4$-alkyl, $C_1$–$C_4$-alkenyl, $C_1$–$C_4$-alkoxy-$C_1$–$C_4$-alkyl, phenyl or $C_1$–$C_3$-alkylphenyl, preferably hydrogen, methyl or phenyl, where in particular $R^4$ is hydrogen if $R^5$ is not hydrogen, and A is an anion, with a compound of the formulae $RSO_3X$, $R^1SO_4X$ or $R^2CO_2X$, where R, $R^1$ and $R^2$ are $C_4$–$C_{20}$-alkyl, preferably $C_{10}$–$C_{18}$-alkyl or substituted aryl, preferably $C_1$–$C_{18}$-alkylphenyl, and X is an alkali metal ion, ammonium ion or hydrogen ion, in the presence of water at elevated temperature.

Suitable compounds of the formulae $RSO_3X$, $R^1SO_4X$ and $R^2CO_2X$ are all generally known and customary alkanesulfonates, paraffinsulfonates, substituted arylsulfonates, alkyl sulfates and fatty acid alkylcarboxylates.

The method according to the invention is preferably carried out by dissolving the nitriles of the formula 1 in water at 50 to 100° C.; preferably 60 to 90° C., in particular 70 to 85° C., to saturation and mixing them with an aqueous solution, saturated in the same temperature range, of the compounds of the formulae $RSO_3X$, $R^1SO_4X$ and $R^2CO_2X$, for example cumenesulfonate, lauryl sulfate or fatty acid alkylcarboxylates. The ammonium nitrile sulfonates, sulfates or carboxylates, which are less soluble than the starting salts, can be obtained as white solids by precipitation. To achieve this, the mixing solution is cooled.

The molar ratio of the compounds of the formulae $RSO_3(X)$, $RSO_4(X)$ and $RCO_2(X)$ and of the nitriles of the formula 1 is in the range from 1:2 to 5:1, preferably 1:1 to 4:1.

In a preferred embodiment, a 40% strength, aqueous clear solution of sodium cumenesulfonate and/or sodium lauryl sulfate is mixed with a 50 to 80% strength aqueous clear solution of cyanomethyltrimethylammonium methylsulfate and/or chloride at the temperatures given above, where the molar ratio of sodium cumenesulfonate or sodium lauryl sulfate to ammonium nitrile chloride or methosulfate is 1:1 to 2:1.

The ammonium nitrile sulfonates, sulfates or carboxylates, which are less soluble than the starting salts, crystallize out at temperatures in the range from 40° C. to 0° C., preferably at about 20° C. and can be filtered off, where necessary recrystallized and dried.

In a further procedure according to the invention, ammonium nitrile with conventional anions according to formula 1 are dissolved in water at 50 to 100° C., preferably 60 to 90° C., in particular 70 to 85° C. and homogeneously mixed with an aqueous solution, which is heated to a temperature within this temperature range, of compounds of the formulae $RSO_3X$, $R^1SO_4X$ or $R^2CO_2X$, for example cumenesulfonate, lauryl sulfate, $C_{12/18}$-alkyl sulfate or fatty acid alkylcarboxylates. The solution is not crystallized, but subjected to a spray-drying in the temperature range given above, where the gas exit temperature is in the range from 100 to 150° C. The resulting white, pulverulent solid is composed of nitrile salts with the anion according to the formulae $RSO_3^-$, $R^1SO_3^-$ or $R^2COO^-$, the starting compounds and alkali metal/ammonium salts with the anion A, where anions and cations are present in random distribution.

In a further preferred embodiment for minimizing the hydrolysis sensitivity, the hygroscopicity, and the liquefaction of ammonium nitrites, ammonium nitrites with conventional anions according to formula 1 are dissolved in water at 50 to 100° C., preferably 60 to 90° C., in particular 70 to 85° C. and homogeneously mixed with an aqueous solution, saturated in the same temperature range, of compounds of the formulae $RSO_3X$, $R^1SO_4X$ or $R^2COOX$, for example cumenesulfonate, lauryl sulfate, $C_{12/18}$-alkyl sulfate, and also with an aqueous solution or dispersion of an inorganic salt, for example $Na_2SO_4$, which may likewise be heated to the given temperatures, and subjected at these temperatures to a spray-drying, where the gas exit temperature is in the range from 100° C. to 150° C. This gives a white, pulverulent solid in the form of a homogeneous mixture with random anion distribution of nitrile salts with the anions $RSO_3^-$, $R^1SO_4^-$ or $R^2COO^-$, the starting compounds and alkali metal/ammonium salts with the amine A, and alkali metal/ammonium sulfate, for example $Na_2SO_4$.

The anion exchange can also be achieved by dry mixing of the ammonium nitrites according to the formula 1, and of the compounds of the formulae $RSO_3X$, $R^1SO_4X$ or $R^2COOX$ in the molar ratio 1:2 to 5:1, preferably 1:1 to 4:1, addition of water and homogenization by mixing, kneading and dispersion of the pasty mixture and subsequent drying.

The above-described anion exchange according to the invention with anions of higher molecular weights achieves a significant reduction in the hygroscopicity and thus a considerable improvement in the storage stability of the ammonium nitriles.

As bleach activator in laundry detergents and cleaners, particular preference is given to ammonium nitrites according to the formula 2

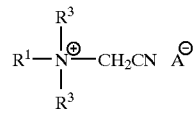

Formula 2 where $R^1$, $R^2$ and $R^3$ are a linear or branched, saturated or unsaturated alkyl group having 1 to 24 carbon atoms, or 2 to 24 carbon atoms, or substituted or unsubstituted benzyl, and A is an anion of the formulae $RSO_3^-$, $R^1SO_4^-$ or $R^2COO^-$, particularly preferably cumenesulfonate and $C_{12/18}$-alcohol sulfate or mixtures of the components.

In order to ensure adequate storage stability and to liberate the bleach-activating action only during the wash operation, it is advantageous to use the ammonium nitrites prepared according to the invention in granulated form. The ammonium nitrites prepared according to the invention can, with or without the addition of a binder, be compressed, compacted and gently comminuted to granule sizes of from 200 to 2000 µm.

Also suitable is a build-up granulation in a mixer, for example in a plowshare mixer, annular bed mixer or intensive mixer with the addition of a binder, in particular an anhydrous binding system, for example a fatty alcohol polyglycol ether.

In a further embodiment, the moist filtercake from the above-described precipitation reaction can be subjected, with or without the addition of a binder, to a shaping granulation through dies in an extruder, or else in annular edge-runner presses, edge runners, optionally with downstream spheronizer.

In the same way, the dried solid substance of the above-described precipitation reaction or the dry powders obtained by spray-drying can be granulated.

Also suitable is a fluidized-bed granulation of an aqueous solution of the mixed salts of the ammonium nitrites prepared by the above-described anion exchange.

In order to avoid fabric and color damage, it is advantageous to coat the granules of the ammonium nitrile salts prepared according to the invention with coating substances.

Suitable coating materials are all film-forming substances, such as waxes, silicones, fatty acids, soaps, anionic surfactants, nonionic surfactants, cationic surfactants, and anionic and cationic polymers, e.g. polyacrylic acids. The use of these coating materials can, inter alia, delay the dissolution behavior in order, in this way, to also prevent interactions between the bleach activator and the enzyme system at the start of the washing process. If the granules according to directions are to be used in machine dishwashing detergents, waxes with melting points of from 40 to 50° C. are primarily suitable for this purpose.

Acidic coating materials increase the storage stability of the granules in percarbonate-containing, highly alkaline formulations and suppress color damage by spotting. Additions of a dye are likewise possible.

The coating materials are generally applied by spraying on the molten coating materials or coating materials dissolved in a solvent. According to the invention, the coating material can be applied in amounts of 0–20% by weight, preferably 1–10% by weight, based on the total weight of the granule core according to the invention.

The products according to the invention are characterized by good storage stability in pulverulent laundry detergent, cleaner and disinfectant formulations. They are ideal for use in heavy-duty detergents, stain-removal salts, machine dishwashing detergents, pulverulent all-purpose cleaners and denture cleaners.

EXAMPLES

Example 1

A 40% strength aqueous solution which comprises 210 g of cyanomethyltrimethylammonium methosulfate was mixed, with stirring, with a 33% aqueous solution which comprises 222 g of sodium cumenesulfonate. The temperatures of the starting solutions were about 30 to 40° C. The mixing solution was cooled with stirring to less than 15° C. During this, a solid was precipitated out. By further cooling the solution to temperatures of about 3 to 5° C., an additional after-precipitation of the solid can be achieved.

The dry solid was analyzed with regard to its hygroscopic properties compared with cyanomethyltrimethylammonium methosulfate (nitrile quat A).

Weight increase at 80% Relative Atmospheric Humidity:

| Time | Nitrile quat A | Precipitation product |
| --- | --- | --- |
| 10 min | 4.9% | 2.22% |
| 30 min | 14.5% | 4.11% |
| 60 min | 24.6% | 5.34% |
| 120 min | 35.1% | 5.86% |
| 130 min | 35.9% (liquid) | 5.75% (solid powder) |

Example 2

10 g of a 58% strength solution of cyanomethyltrimethylammonium chloride in water were admixed with 48 g of a 40% strength aqueous solution of sodium cumenesulfonate and heated to 80° C. The clear solution was sprayed in a mini spray-tower from Büchi to give a dry powder (residual moisture <1% by weight). The spraying conditions are:

| Inlet temperature: | 220° C. |
| --- | --- |
| Outlet temperature: | 111° C. |

-continued

| Amount of spray gas to the nozzle: | 600 l/h |
| --- | --- |
| Dosing pump capacity: | 9 ml/min |

The resulting powder showed a mass increase during storage under moist conditions (12 h, 78% relative atmospheric humidity) of 30%. The powder remains stable and shows no visible change in the external form.

Example 3

13.4 g of cyanomethyltrimethylammonium chloride (nitrile quat B) were dissolved in 13.4 g of water and admixed with 44 g of sodium cumenesulfonate as 40% strength aqueous solution, and heated to 60 to 70° C. The resulting solution was dried under reduced pressure. The resulting powder was dried at 80% relative atmospheric humidity and the weight increase (in %) was observed.

| Time | Nitrile quat B | Evaporation product example 3 |
| --- | --- | --- |
| 44 h | 95% (liquid) | 25% (solid) |

Example 4

A compact was prepared from the nonhygroscopic precipitation product prepared in example 1 by means of dry compression. The compact is coated for further protection with 10% stearic acid. To test the storage stability of the granules, they were incorporated into a detergent formulation in an amount of 5%, the formulation comprising all of the customary detergent ingredients. The samples prepared in this way were stored in sealed vessels for up to 4 weeks at T=38° C. and ambient humidity. At regular intervals, the active ingredient present in the samples is determined.

The following values for active ingredient retention (in %) were ascertained:

| Time | Nitrile quat A | Precipitation product |
| --- | --- | --- |
| 0 days | 100% | 100% |
| 10 days | 83% | 95% |
| 21 days | 30% | 95% |
| 28 days | 21% | 85% |

Example 5

21 g of cyanomethyltrimethylammonium methosulfate were dissolved in water and admixed with 59.8 [lacuna] of sodium $C_{12/14}$-alkyl sulfate as aqueous solution. This mixture was dried at 60 to 70° C. The resulting powder was stored at 80% relative atmospheric humidity. The mass increase after 44 h was 26%. The powder remains stable and does not show any visible change in the external form.

What is claimed is:

1. A method for producing an hydrolysis-stable ammonium nitrile comprising reacting a first compound of the formula 1

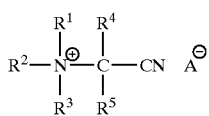

Formula 1 in which $R^1$, $R^2$, $R^3$ are identical or different and are linear or branched $C_1$–$C_{24}$-alkyl groups, $C_2$–$C_{24}$-alkenyl groups or are $C_1$–$C_4$-alkoxy-$C_1$–$C_4$-alkyl groups, substituted or unsubstituted benzyl, or in which $R^1$ and $R^2$ together with the nitrogen atom to which they are bonded form a ring having 4 to 6 carbon atoms, which may be substituted by $C_1$–$C_5$-alkyl, $C_1$–$C_5$-alkoxy, $C_1$–$C_5$-alkanoyl, phenyl, amino, ammonium, cyano, cyanamino, chlorine or bromine and which can contain in addition to the nitrogen atom, instead of carbon atoms, one or two oxygen or nitrogen atoms, a group N—$R^6$ or a group $R^3$—N—$R^6$, in which $R^6$ is hydrogen, $C_1$- to $C_5$-alkyl, $C_2$- to $C_5$-alkenyl, $C_2$–$C_5$-alkynyl, phenyl, $C_7$–$C_9$-aralkyl, $C_5$–$C_7$-cycloalkyl, $C_1$–$C_6$-alkanoyl, cyanomethyl or cyano, $R^4$ and $R^5$ are hydrogen, $C_1$–$C_4$-alkyl, $C_1$–$C_4$-alkenyl, $C_1$–$C_4$-alkoxy-$C_1$–$C_4$-alkyl, phenyl or $C_1$–$C_3$-alkylphenyl, preferably hydrogen, methyl or phenyl, where in particular $R^4$ is hydrogen if $R^5$ is not hydrogen, and A is an anion, with a second compound of the formulae $RSO_3X$, $R^7SO_4X$ or $R^8CO_2X$, where R, $R^7$ and $R^8$ are $C_4$–$C_{20}$-alkyl or substituted aryl and X is an alkali metal ion, ammonium ion or hydrogen ion, in the presence of water at elevated temperature.

2. The method as claimed in claim 1, where A is selected from the group consisting of chloride, bromide, iodide, fluoride, sulfate, hydrogen sulfate, carbonate, hydrogen carbonate, phosphate, mono- and dihydrogen phosphate, pyrophosphate, metaphosphate, nitrate, methylsulfate, phosphonate, methylphosphonate, methanedisulfonate, methylsulfonate, ethanesulfonate, and mixtures thereof.

3. The method of claim 1, wherein the second compound is an alkali metal salt or ammonium salt of a compound selected from the group consisting of p-toluenesulfonate, dodecylbenzenesulfonate, $C_8$–$C_{18}$-ether sulfate, sodium sulfate, $C_8$–$C_{18}$-alkylcarboxylate, and the mixtures thereof.

4. The method of claim 1, wherein the second compound is an alkali metal salt or ammonium salt of cumenesulfonate.

5. The method of claim 1, wherein the second compound is an alkali metal salt or ammonium salt of lauryl sulfate and/or $C_8$–$C_{18}$-alcohol sulfate.

6. The method of claim 1, wherein the elevated temperature is 50 to 100° C.

7. The method of claim 1, in which the first compound is dissolved in water, and reacted with an aqueous solution of the second compound in a molar ratio of the second compound to the first compound ranging from 1:2 to 5:1 to form a reaction mixture.

8. The method of claim 7, further comprising cooling the reaction mixture to precipitate the hydrolysis-stable ammonium nitrile.

9. The method of claim 7, further comprising spray-drying the reaction mixture to recover the hydrolysis-stable ammonium nitrile.

10. The method of claim 9, further comprising granulating the hydrolysis-stable ammonium nitrile into granules and coating the granules with a coating substance.

11. The method of claim 1, wherein with reference to the second component R, $R^7$ and $R^8$ are $C_{10}$–$C_{18}$-alkyl or $C_1$–$C_{18}$-alkylphenyl.

12. The method of claim 1, wherein R4 and R5 are hydrogen, methyl, or phenyl.

13. The method of claim 7, wherein the molar ratio of the second compound to the first compound ranges from 1.1 to 4:1.

* * * * *